US009861295B2

(12) United States Patent
Powell et al.

(10) Patent No.: US 9,861,295 B2
(45) Date of Patent: Jan. 9, 2018

(54) SYSTEM AND METHOD FOR SURGICAL PLANNING AND NAVIGATION TO FACILITATE PLACEMENT OF A MEDICAL DEVICE WITHIN A TARGET REGION OF A PATIENT

(71) Applicant: Autonomic Technologies, Inc., Redwood City, CA (US)

(72) Inventors: Ryan Powell, Sunnyvale, CA (US); Brinda Ramachandran, San Jose, CA (US); Benjamin David Pless, Atherton, CA (US); Anthony Caparso, San Mateo, CA (US); Kathryn Rosenbluth, San Fransisco, CA (US)

(73) Assignee: AUTONOMIC TECHNOLOGIES, INC., Redwood City, CA (US)

( * ) Notice: Subject to any disclaimer, the term of this patent is extended or adjusted under 35 U.S.C. 154(b) by 67 days.

(21) Appl. No.: 14/283,420

(22) Filed: May 21, 2014

(65) Prior Publication Data
US 2014/0350389 A1 Nov. 27, 2014

Related U.S. Application Data

(60) Provisional application No. 61/825,767, filed on May 21, 2013.

(51) Int. Cl.
*A61B 5/05* (2006.01)
*A61B 5/06* (2006.01)
(Continued)

(52) U.S. Cl.
CPC .............. *A61B 5/066* (2013.01); *A61B 6/032* (2013.01); *A61B 6/466* (2013.01); *A61B 6/501* (2013.01);
(Continued)

(58) Field of Classification Search
CPC .......... A61B 19/5244; A61B 2019/524; A61B 2019/5265; A61B 5/066; A61B 6/032;
(Continued)

(56) References Cited

U.S. PATENT DOCUMENTS

2001/0041835 A1* 11/2001 Front ..................... A61B 6/032
600/429
2008/0123922 A1* 5/2008 Gielen .................... A61B 5/06
382/131
(Continued)

*Primary Examiner* — Elmer Chao
(74) *Attorney, Agent, or Firm* — Tarolli, Sundheim, Covell & Tummino LLP

(57) ABSTRACT

One aspect of the present disclosure relates to a system that can facilitate delivery of a medical device in proximity to a target region within a patient's body. Data representing an image of a portion of the patient's body can be received. Based on the data representing the image, a first three dimensional (3D) model of the medical device can be generated. A second 3D model of the medical device can be fitted within the first 3D model at a location in proximity to the target region to create a combined 3D model. A two dimensional (2D) projection of the combined 3D model can be created. In some instances, the 2D projection can be used to facilitate delivery of a medical device in proximity to the target region within a patient's body.

14 Claims, 7 Drawing Sheets

(51) Int. Cl.
*A61B 6/03* (2006.01)
*A61B 6/00* (2006.01)
A61B 34/10 (2016.01)
A61B 90/00 (2016.01)

(52) U.S. Cl.
CPC ............ *A61B 6/5223* (2013.01); *A61B 34/10* (2016.02); *A61B 2034/104* (2016.02); *A61B 2090/367* (2016.02)

(58) Field of Classification Search
CPC ....... A61B 6/466; A61B 6/501; A61B 6/5223; A61B 34/10; A61B 2034/104; A61B 2090/367
See application file for complete search history.

(56) References Cited

U.S. PATENT DOCUMENTS

| | | | |
|---|---|---|---|
| 2009/0088634 A1* | 4/2009 | Zhao ..................... | B25J 9/1689 600/427 |
| 2012/0063655 A1 | 3/2012 | Dean et al. | |
| 2012/0289825 A1* | 11/2012 | Rai ....................... | A61B 6/463 600/425 |
| 2012/0323214 A1* | 12/2012 | Shantha .................. | A61N 1/30 604/501 |
| 2013/0172906 A1* | 7/2013 | Olson ................ | A61B 19/2203 606/130 |

\* cited by examiner

SYSTEM AND METHOD FOR SURGICAL PLANNING AND NAVIGATION TO FACILITATE PLACEMENT OF A MEDICAL DEVICE WITHIN A TARGET REGION OF A PATIENT

RELATED APPLICATIONS

This application claims the benefit of U.S. Provisional Application No. 61/825,767, filed May 21, 2013, entitled "Surgical Planning and Navigation to Facilitate Delivery of a Neurostimulator into the Pterygopalatine Fossa," the entirety of which is hereby incorporated by reference for all purposes.

TECHNICAL FIELD

The present disclosure relates generally to surgical planning and, more specifically, to systems and methods that can employ surgical planning to facilitate placement of a medical device within a target region of a patient.

BACKGROUND

Primary headaches (e.g., cluster headaches, tension headaches, chronic migraines, etc.) are debilitating ailments that afflict millions of individuals worldwide. By definition, a primary headache is idiopathic and non-specific with many possible causes. Examples of possible causes for primary headaches include: trauma, vascular defects, autoimmune deficiencies, degenerative conditions, infections, drug and medication-induced causes, inflammation, neoplastic conditions, metabolic-endocrine conditions, iatrogenic conditions, musculoskeletal conditions, and myofacial causes. While primary headaches can be treated with painkillers to varying levels of success, in many situations, the headache pain can persist post-treatment.

Recent clinical studies in the treatment of headache pain have targeted therapies to the sphenopalatine (pterygopalatine) ganglion (SPG). The SPG is a collection of nerves (e.g., parasympathetic neurons that innervate the middle cerebral and anterior cerebral blood vessels, the facial blood vessels, and the lacrimal glands) located within the pterygopalatine fossa (PPF), a boney cavity deep within the midface. The SPG is a complex neural ganglion with multiple connections (including autonomic connections, sensory connections, and motor connections). One or more of these connections may contribute to the pathogenesis of primary headaches.

Various clinical approaches have been used to modulate the function of SPG for the treatment of primary headaches. These approaches vary from minimally invasive procedures (e.g., transnasal anesthetic blocks) to procedures with greater invasiveness (e.g., surgical ganglionectomy). Other procedures of varying invasiveness include surgical anesthetic injections, ablations, gamma knife procedures, and cryogenic surgery. Although most of these procedures can provide short term relief to the pain of primary headaches (e.g., from days to months), this relief is often temporary.

SUMMARY

The present disclosure relates generally to surgical planning and more specifically to systems and methods that can employ surgical planning to facilitate placement of the medical device in proximity to the target region within the patient's body.

In one aspect, the present disclosure can include a system facilitates delivery of a medical device in proximity to a target region within a patient's body. The system can include a non-transitory memory storing computer-executable instructions and a processor that executes the computer-executable instructions to at least: receive data representing an image of a portion of the patient's body; generate a first three dimensional (3D) model of the portion of the patient's body based on the data representing the image; fit a second 3D model of the medical device within the first 3D model at a location in proximity to the target region to create a combined 3D model; and create a two dimensional (2D) projection of the combined 3D model. In some instances, the 2D projection can be used to facilitate delivery of a medical device in proximity to the target region within a patient's body In another aspect, the present disclosure can include a method for delivering of a medical device in proximity to a target region within a patient's body. The method can include steps that can be performed by a system that includes a processor. The steps can include: receiving data representing an image of a portion of the patient's body; generating a first three dimensional (3D) model of the portion of the patient's body based on the data representing the image; fitting a second 3D model of the medical device within the first 3D model at a location in proximity to the target region to create a combined 3D model; and creating a two dimensional (2D) projection of the combined 3D model. In some instances, the 2D projection can be used to facilitate delivery of a medical device in proximity to the target region within a patient's body In a further aspect, the present disclosure can include a non-transitory computer-readable device storing instructions executable by an associated processor to perform operations that facilitate delivery of a medical device in proximity to a target region within a patient's body. The operations can include: receiving data representing an image of a portion of the patient's body; generating a first three dimensional (3D) model of the portion of the patient's body based on the data representing the image; fitting a second 3D model of the medical device within the first 3D model at a location in proximity to the target region to create a combined 3D model; and creating a two dimensional (2D) projection of the combined 3D model. In some instances, the 2D projection can be used to facilitate delivery of a medical device in proximity to the target region within a patient's body.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

I. Definitions

Figure 1:
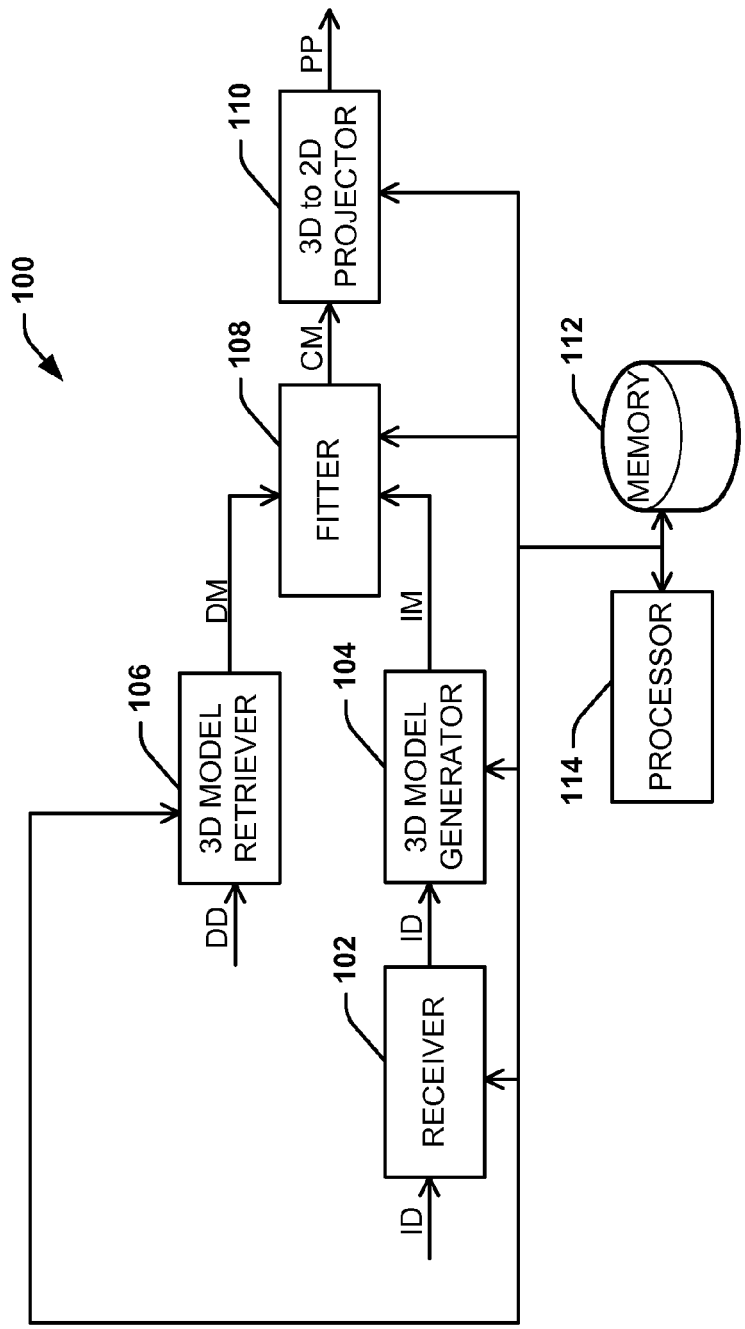
FIG. 1 is a schematic block diagram showing a system that facilitates delivery of a medical device to a location in proximity to a target region within a patient's body, in accordance with an aspect of the present disclosure.

In the context of the present disclosure, the singular forms "a," "an" and "the" can also include the plural forms, unless the context clearly indicates otherwise. The terms "comprises" and/or "comprising," as used herein, can specify the presence of stated features, steps, operations, elements, and/or components, but do not preclude the presence or addition of one or more other features, steps, operations, elements, components, and/or groups. As used herein, the term "and/or" can include any and all combinations of one or more of the associated listed items. Additionally, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

As used herein, the term "target region" can refer to location within the patient's body that includes an idealized location for placement of the medical device. The idealized location can be a location within the body where the medical device would benefit the patient. For example, for the treatment of primary headache pain, the medical device (a neurostimulator) can be implanted within the craniofacial region in proximity to the target region (sphenopalatine (pterygopalatine) ganglion (SPG)).

As used herein, the term "medical device" can refer to any device that can be located within a patient's body. In some instances, the medical device can be an implantable device, such as: a neurostimulator, a device configured to monitor a physiological response of the patient's tissue, a therapeutic agent delivery device, a bone graft, and a sensor. In other instances, the medical device can be a removable device, such as a surgical instrument.

As used herein, the term "neurostimulator" (or "neural stimulator") can refer to an implantable device configured to deliver stimulation (e.g., electrical stimulation, magnetic stimulation, etc.) to one or more nerve within the patient's body. The one or more nerves can be within the central nervous system or the peripheral nervous system. In some instances, the neurostimulator can be a battery powered pulse generator device.

As used herein, the term "primary headache" can refer to an idiopathic and non-specific type of headache that is not caused by another disease. Examples of primary headaches include: cluster headaches, tension headaches, and chronic migraines.

As used herein, the term "ganglion" can refer to a structure containing a number of nerve cell bodies. In some instances, a ganglion can form a mass of nerve tissue.

As used herein, the term "image" can refer to a visual representation of the interior of a patient's body. In some instances, an image can be a three dimensional (3D) image that captures an image in three dimensions. One example of a 3D image is a 3D computed tomography (CT) image. In other instances, the image can be a two dimensional (2D) image. One example of a 2D image is a 2D intraoperative fluoroscopic image. In some instances the image can be a real time image (e.g., a 2D intraoperative fluoroscopic image). In other instances, the image can be created before a surgical procedure (e.g., a 3D CT image).

As used herein, the term "3D model" can refer to a mathematical representation of a three dimensional surface of an object. In some instances, the 3D model can be constructed by a specialized software program. One example of a specialized software program that can be used to create a 3D model from a 2D image is MIMICS® by Materialise of Leuven, Belgium.

As used herein, the term "two dimensional (2D) projection" refers to a means of representing a 3D object in two dimensions. In some instances, different views of the projection can be created to account for all of the axes of the 3D object. An example of a projection can be a digitally reconstructed radiograph (DRR).

As used herein, the term "proximity" or "close proximity" can refer to a distance from the target region less than about 50 mm. In some instances, the distance from the target region can be less than 25 mm. In other instances, the distance from the target region can be less than 10 mm.

As used herein, the term "real time" can refer to a system or method in which input data is processed quickly (e.g., within milliseconds) so that feedback related to the data it is available immediately or almost immediately (e.g., within milliseconds). Accordingly, a "real time image" can correspond to an image that is displayed within milliseconds from the time when it was recorded.

As used herein, the term "medical professional" can refer to any person involved the conducting a procedure (e.g., a surgical procedure) involving a medical device including, but not limited to, physicians, medical students, nurse practitioners, nurses, and other operating room staff.

As used herein, the term "patient" can refer to any warm-blooded organism including, but not limited to, a human being, a pig, a rat, a mouse, a dog, a cat, a goat, a sheep, a horse, a monkey, an ape, a rabbit, a cow, etc. The terms "patient" and "subject" can be used interchangeably herein.

II. Overview

The present disclosure relates generally to surgical planning and more specifically to systems and methods that can employ surgical planning to facilitate placement of the medical device in proximity to the target region within the patient's body. In some instances, the surgical planning can facilitate delivery of an implantable neurostimulator in the cranio-facial region in proximity to the sphenopalatine (pterygopalatine) ganglion (SPG), which is located within the pterygopalatine fossa. Implanting the neurostimulator in proximity to the SPG can provide a more permanent relief from primary headache pain than traditional clinical approaches that can provide short term relief from the primary headache pain.

The systems and methods of the present disclosure can facilitate delivery of a medical device (e.g., the neurostimulator) in proximity to the target region (e.g., the SPG) within a patient's body. Data representing an image of a portion of the patient's body can be received. Based on the data representing the image, a first three dimensional (3D) model of the medical device can be generated. A second 3D model of the medical device can be fitted within the first 3D model at a location in proximity to the target region to create a combined 3D model. A two dimensional (2D) projection of the combined 3D model can be created. In some instances, the 2D projection can be compared to a real time intraoperative 2D image to facilitate the placement of the medical device in proximity to the target region.

III. Systems

One aspect of the present disclosure can include a system that can facilitate delivery of a medical device to a location in proximity to a target region within a patient's body. The system can utilize a three dimensional (3D) to two dimensional (2D) conversion to facilitate the delivery. For example, data representing an image of a portion of the patient's body can be received. Based on the data representing the image, a first three dimensional (3D) model of the medical device can be generated. A second 3D model of the medical device can be fitted within the first 3D model at a location in proximity to the target region to create a combined 3D model. A two dimensional (2D) projection of the combined 3D model can be created. In some instances, the 2D projection can be compared to a real time intraoperative 2D image to facilitate the placement of the medical device in proximity to the target region.

Figure 3:
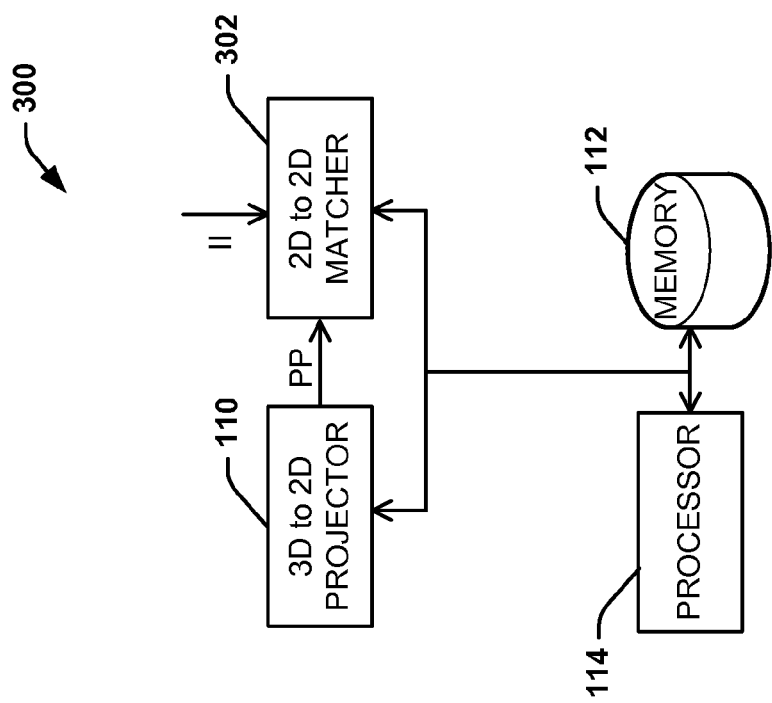
FIG. 3 is a schematic block diagram showing a system that can match the projection as determined by the system in FIG. 1 to a real time intraoperative image.
Figure 4:
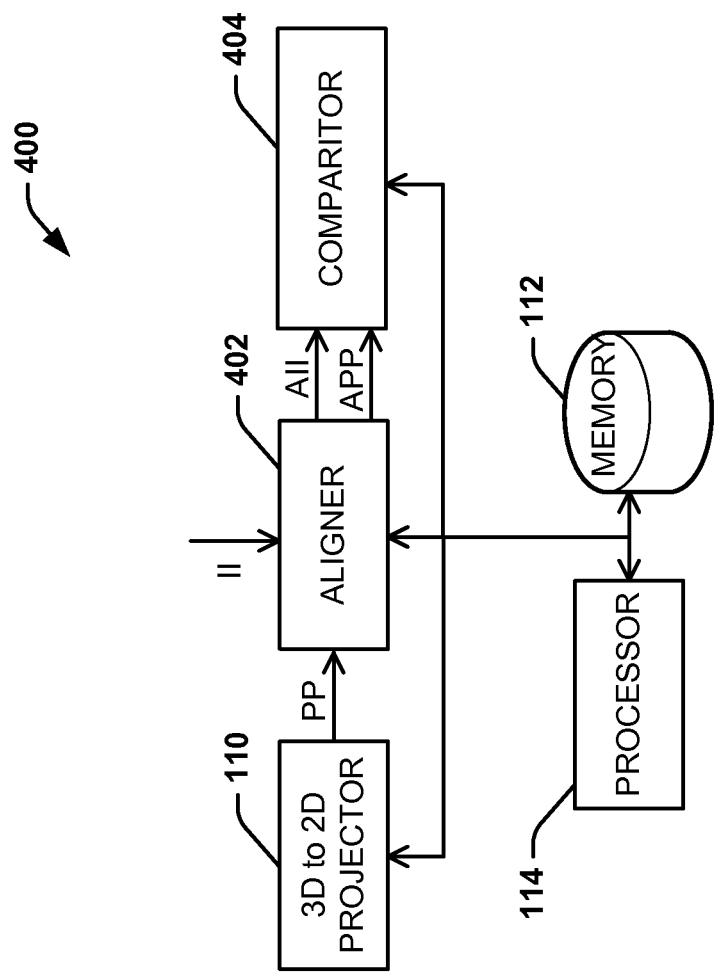
FIG. 4 is a schematic block diagram showing a system that can align the projection as determined by the system in FIG. 1 with the real time intraoperative image.

FIG. 1 illustrates an example of a system 100 that can facilitate delivery of a medical device to a location in proximity to a target region within a patient's body in an aspect of the present disclosure. FIG. 1, as well as associated FIGS. 3-4, are schematically illustrated as block diagrams with the different blocks representing different components. The functions of one or more of the components can be implemented by computer program instructions. These computer program instructions can be provided to a processor of a general purpose computer, special purpose computer, and/or other programmable data processing apparatus to produce a machine, such that the instructions, which execute via the processor of the computer and/or other programmable data processing apparatus, create a mechanism for implementing the functions of the components specified in the block diagrams.

These computer program instructions can also be stored in a non-transitory computer-readable memory that can direct a computer or other programmable data processing apparatus to function in a particular manner, such that the instructions stored in the non-transitory computer-readable memory produce an article of manufacture including instructions, which implement the function specified in the block diagrams and associated description.

The computer program instructions can also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions of the components specified in the block diagrams and the associated description.

Accordingly, the system 100 described herein can be embodied at least in part in hardware and/or in software (including firmware, resident software, micro-code, etc.). Furthermore, aspects of the system 100 can take the form of a computer program product on a computer-usable or computer-readable storage medium having computer-usable or computer-readable program code embodied in the medium for use by or in connection with an instruction execution system. A computer-usable or computer-readable medium can be any non-transitory medium that is not a transitory signal and can contain or store the program for use by or in connection with the instruction or execution of a system, apparatus, or device. The computer-usable or computer-readable medium can be, for example but not limited to, an electronic, magnetic, optical, electromagnetic, infrared, or semiconductor system, apparatus or device. More specific examples (a non-exhaustive list) of the computer-readable medium can include the following: a portable computer diskette; a random access memory; a read-only memory; an erasable programmable read-only memory (or Flash memory); and a portable compact disc read-only memory.

As shown in FIG. 1, one aspect of the present disclosure can include a system 100 configured to facilitate delivery of a medical device to a location in proximity to a target region within a patient's body. The system 100 can utilize a three dimensional (3D) to two dimensional (2D) conversion to facilitate the delivery.

Figure 2:
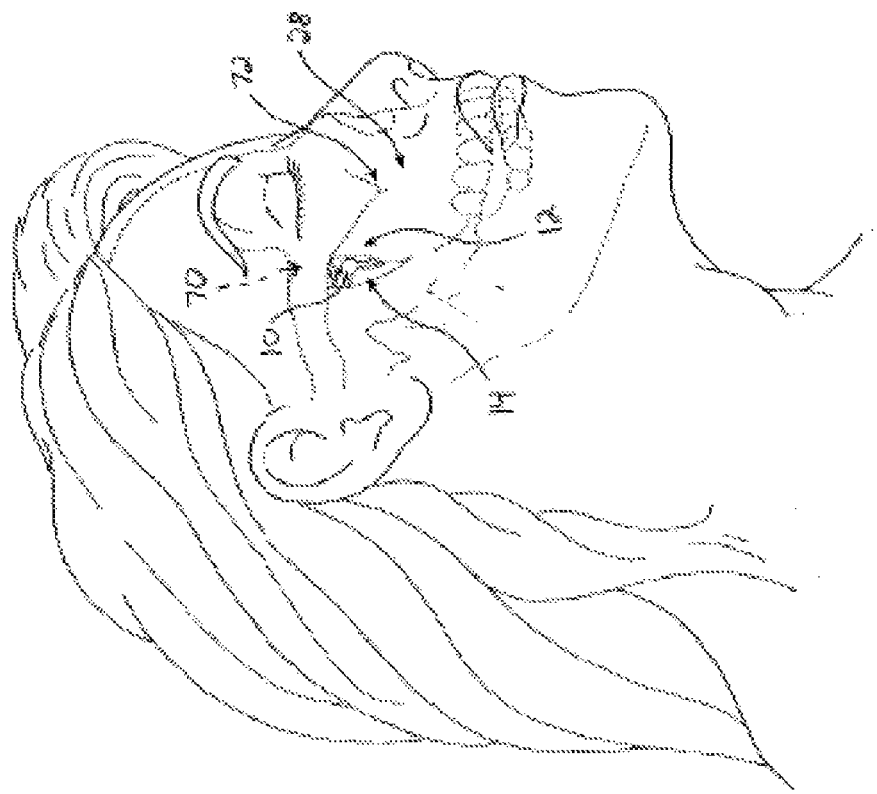
FIG. 2 is a schematic illustration showing the position of the sphenopalatine ganglion (SPG) lying within the pterygopalatine fossa.

System 100 can be described with respect to placement of a neurostimulator in proximity to a patient's sphenopalatine (pterygopalatine) ganglion (SPG) within the cranio-facial region. FIG. 2 is a schematic illustration showing the position of a sphenopalatine ganglion (SPG) 10 lying within the pterygopalatine fossa (PPF) 14 on the left side of a patient's head. While SPGs are located on both sides of the head, only the left side is illustrated in FIG. 2 for simplicity of illustration and explanation.

The SPG 10 is located behind the posterior maxilla 12 in the PPF 14, posterior to the middle nasal turbinate (not shown in detail). The PPF 14 is bounded anteriorly by the maxilla, posteriorly by the medial plate of the pterygoid process and greater wing of the sphenoid process, medially by the palatine bone, and superiorly by the body of the sphenoid process. The lateral border of the PPF 14 is the pterygomaxillary fissure, which opens to the infratemporal fossa.

The SPG 10 is part of the parasympathetic nervous system (PNS), which is a division of the autonomic nervous system. Generally, the autonomic nervous system innervates numerous pathways within the human body and consists of two divisions: the sympathetic nervous system (SNS) and the PNS. The SNS and PNS are antagonistic in their action, balancing the other system's effects within the body. The SNS usually initiates activity within the body, preparing the body for action, while the PNS primarily counteracts the effects of the SNS.

As part of the PNS, the SPG 10 has parasympathetic nerve fibers forming synapses within the ganglion. However, the SPG 10 also has fibers passing through the ganglion and not synapsing within the ganglion, including sympathetic nerve fibers, sensory nerve fibers, and motor nerve fibers.

For example, the maxillary branch of the trigeminal nerve and the nerve of the pterygoid canal (also known as the vidian nerve which is formed by the greater and deep petrosal nerves) send neural projections to the SPG 10. The fine branches from the maxillary nerve (pterygopalatine nerves) form the sensory component of the SPG 10. These nerve fibers pass through the SPG 10 and do not synapse. The greater petrosal nerve carries the preganglionic parasympathetic axons from the superior salivary nucleus, located in the pons, to the SPG 10. These fibers synapse onto the postganglionic neurons within the SPG 10. The deep petrosal nerve connects the superior cervical sympathetic ganglion to the SPG 10 and carries postganglionic sympathetic axons that again pass through the SPG without any synapsing in the SPG.

The parasympathetic activity of the SPG 10 is mediated through the greater petrosal nerve (not shown), while the sympathetic activity of the SPG is mediated through the deep petrosal nerve (not shown), which is essentially an extension of the cervical sympathetic chain (not shown). Sensory sensations generated by or transmitted through the SPG 10 can include: sensations to the upper teeth, feelings of foreign bodies in the throat, and persistent itching of the ear. The SPG 10 can transmit sensory information, including pain, to the trigeminal system via the maxillary division and ophthalmic division (not shown).

Although system 100 is described with respect to the placement of a neurostimulator in proximity to a patient's SPG for the treatment of headache pain, system 100 can be utilized to facilitate the placement of any medical device in proximity to any target region within the patient's body. System 100 can be employed to assist in the treatment of a variety of chronic or acute medical conditions. Examples of such medical conditions can include: pain (e.g., headache and/or facial pain), movement disorders, epilepsy, cerebrovascular diseases, autoimmune diseases, sleep disorders, autonomic disorders, neurological disorders, urinary bladder disorders, abnormal metabolic states, disorders of the muscular system, and neuropsychiatric disorders. In addition, system 100 can assist in surgical planning and/or navigation for a surgical procedure, in which any implantable device is inserted into the body and in which bone landmarks, identified via intraoperative imaging (e.g., fluoroscopy), are used to determine accurate placement of the implantable device. Examples of medical devices can include: a neurostimulator, a device configured to monitor a physiological response of the patient's tissue, a therapeutic agent delivery device, a sensor, and a surgical instrument.

Referring again to FIG. 1, the system 100 can include components that can facilitate the delivery of the medical device to the target region, including at least a receiver 102, a 3D model generator 104, a 3D model retriever 106, a fitter 108, and a 3D to 2D projector 110. One or more of the components can include instructions that are stored in a non-transitory memory 112 and executed by a processor 114. Each of the components can be in a communicative relationship with one or more of the other components, the processor 114, and/or the non-transitory memory 112 (e.g., via a direct or indirect electrical, electromagnetic, optical, or other type of wired or wireless communication) such that an action from the respective component causes an effect on one or more of the other components.

The receiver 102 can be configured to receive data representing an image (ID) of a portion of the patient's body that includes the target region. In some instances, the image can be a standard fine resolution (e.g., less than 1 mm slice) computed tomography (CT) image of the portion of the patient's body. For example, the portion of the patient's body can include a portion of the patient's skull. When the target region is the SPG, the portion of the patient's skull can extend from the lower maxilla to the top of the frontal sinus including the entire head of the patient, including at least: the anterior maxilla (element 28 of FIG. 2), the posterior maxilla (element 12 of FIG. 2), the maxillary sinus, the zygoma (element 70 of FIG. 2), the PPF (element 14 of FIG. 2), and the pterygoid process.

In some instances, the receiver 102 can perform any required preprocessing of the data representing the image (ID), such as noise removal and filtering. After the preprocessing, the receiver 102 can pass the data representing the image (ID) to the 3D model generator 104.

The 3D model generator 104 can generate a 3D model (IM) of the portion of the patient's body represented in the image from the data representing the image (ID). In some instances, the 3D model generator 104 can utilize a commercially available software package to process the data representing the image (ID) and generate the 3D model (IM) of the portion of the patient's body represented in the image.

Before, after, or current to the generation of the 3D model (IM) of the portion of the patient's body by the 3D model generator 104, the 3D model retriever 106 can receive data related to the medical device (DD). For example, the data related to the medical device (DD) can include the type of device, the size of the device, the size of components of the device, the orientation of the device, the angle of the device, etc. In some instances, the 3D model retriever 106 can generate a 3D model of the medical device (DM) based on the data related to the medical device (DD). In other instances, the 3D model retriever 106 can retrieve a 3D model of the medical device (DM) from a library including 3D models of medical devices. In some cases, the 3D model retriever 106 can edit the retrieved 3D model of the medical device to account for features of the device data (DD) (e.g., the 3D model retriever 106 can retrieve a neurostimulator with different lead sizes than the leads of the neurostimulator that will be implanted into the patient and edit the leads to represent the actual device).

The fitter 108 can receive the 3D model of the portion of the patient's body represented in the image (IM) from the 3D model generator 104 and the 3D model of the medical device (DM) from the 3D model retriever 106. The fitter 108 can place and/or fit the 3D model of the medical device (DM) within the 3D model of the portion of the patient's body represented in the image (IM) at a location in proximity to the target region to create a combined 3D model (CM). For example, the fitter 108 can utilize one or more reference points common to both the 3D model of the portion of the patient's body represented in the image (IM) and the 3D model of the medical device (DM) to facilitate the fitting.

In some instances, the fitter 108 can fit the 3D model of the medical device (DM) to a plurality of different positions (also referred to as interim positions) within the 3D model of the portion of the patient's body represented in the image (IM). For example, the plurality of different positions can correspond to different sizes of the medical device, different placements of the surgical incision, different navigations through the portion of the patient's body, and/or different trajectories of the pathway from the surgical incision to the different positions.

The 3D to 2D projector 110 can receive the combined 3D model (CM) and create a 2D projection (PP) of the combined 3D model. In some instances, the 2D projection can include a plurality of 2D images corresponding to a complete representation of the 3D model. The 2D projection (PP) can include a plurality of projections corresponding to a rotation of the combined 3D model (CM) rotated to different angles and/or different orientations. For example, the 2D projection (PP) can be rotated to provide views, including at least an anterior-posterior (AP) view and a lateral (profile) view. In some instances, when the image or the portion of the patient's body is a CT image, the 2D projection (PP) can be a digitally reconstructed radiograph (DRR). For example, a DRR can be created using a software program, such as the open source Visualization Toolkit.

A surgeon can utilize the 2D projection (PP) for navigation and/or delivery of the medical device to the target region. For example, the 2D projection (PP) can include one or more bone landmarks. In some instances, the 2D projection can act as a guide or map for the surgeon in the placement of the medical device. In other instances, systems 300 and 400 as illustrated in FIGS. 3 and 4 can facilitate the navigation and delivery of the device to a planned position in proximity to the target region.

Systems 300 and 400 can utilize a real time intraoperative 2D image (II) to facilitate the navigation and delivery of the device. For example the real time intraoperative 2D image (II) can be a fluoroscopic image taken by a fluoroscopic C-arm during surgery. The 2D projection (PP) and the real time intraoperative 2D image (II) can each include one or more bone landmarks. For example, in cases where the target region is the SPG, the bone landmarks can include the PPF, the infraorbital rims, the nasal septum, the palatal roof, and/or the sphenoid sinus. These common landmarks can allow the surgeon to visualize the correct surgical approach and trajectory for placing medical device in proximity to the target region.

FIG. 3 illustrates a system 300 that can match the 2D projection (PP) to a real time 2D intraoperative image (II). The system can include the 3D to 2D projector 110 that can provide the 2D projection (PP) to the 2D to 2D matcher 302. The 2D to 2D matcher 302 can match the real time 2D intraoperative image (II) to the 2D projection (PP). The 2D to 2D matcher 302 can correlate the 2D projection (PP) to the real time 2D intraoperative image (II). For example, the matching and/or correlation can be accomplished using one or more bone landmarks.

In some instances, the 2D projection (PP) and the real time 2D intraoperative image (II) can both be displayed to facilitate comparison. The comparison can tell how close the actual medical device position is to the planned position in proximity to the target region. In some instances, the 2D projection (PP) and the real time 2D intraoperative image (II) can be displayed as separate images. For example, the two images can be displayed side-by-side. In other instances, the 2D projection (PP) and the real time 2D intraoperative image (II) can be displayed with one image overlaid on the other image.

FIG. 4 illustrates a system 400 that can facilitate the display of the overlaid display of the 2D projection (PP) and the real time 2D intraoperative image (II). The system can include the 3D to 2D projector 110 that can provide the 2D projection (PP) to the aligner 402, which can also receive the real time 2D intraoperative image (II). The aligner 402 can align the real time 2D intraoperative image (II) to the 2D projection (PP) and/or the 2D projection (PP) to the real time 2D intraoperative image (II). The alignment can be based on one or more bone landmarks that are present in both the 2D projection (PP) and the real time 2D intraoperative image (II). For example, the aligner 402 can rotate the combined 3D model (CM) in three dimensions to create a second 2D projection to match a 2D fluoroscopic image of the portion of the patient's body. In this case, each different 2D projection (PP) can correspond to a different orientation, and each of the different 2D projections can be fit by the aligner 402 to the real time 2D intraoperative image (II). This can facilitate the matching of the orientation of the 2D projection (APP) to the real time 2D intraoperative image (AII).

The aligner 402 can output the aligned real time 2D intraoperative image (AII) and 2D projection (APP). A comparator 404 can compare the planned location in proximity to the target region of the 2D projection (APP). Based on the comparison, the comparator 404 can output a graphic that indicates that the planned position has been reached, the number of millimeters until the planned position is reached, and/or a trajectory to reach the planned location.

In some instances, a real time 2D intraoperative image (II) with the actual medical device in the patient's body can be created during the surgical procedure and back projected onto the 3D combined model (CM) or the 3D model of the portion of the patient's body represented in the image (IM) to transfer the location of the medical device from the real time 2D intraoperative image (II) to the 3D combined model (CM) or the 3D model of the portion of the patient's body represented in the image (IM). The 3D model of the medical device (DM) can be displayed at the actual location of the medical device to facilitate delivery of the medical device to the planned position in proximity to the target region.

IV. Methods

Another aspect of the present disclosure can include methods can facilitate delivery of a medical device to a location in proximity to a target region within a patient's body. The system can utilize a three dimensional (3D) to two dimensional (2D) conversion to facilitate the delivery. For example, data representing an image of a portion of the patient's body can be received. Based on the data representing the image, a first three dimensional (3D) model of the medical device can be generated. A second 3D model of the medical device can be fitted within the first 3D model at a location in proximity to the target region to create a combined 3D model. A two dimensional (2D) projection of the combined 3D model can be created. In some instances, the 2D projection can be compared to a real time intraoperative 2D image to facilitate the placement of the medical device in proximity to the target region.

Figure 5:
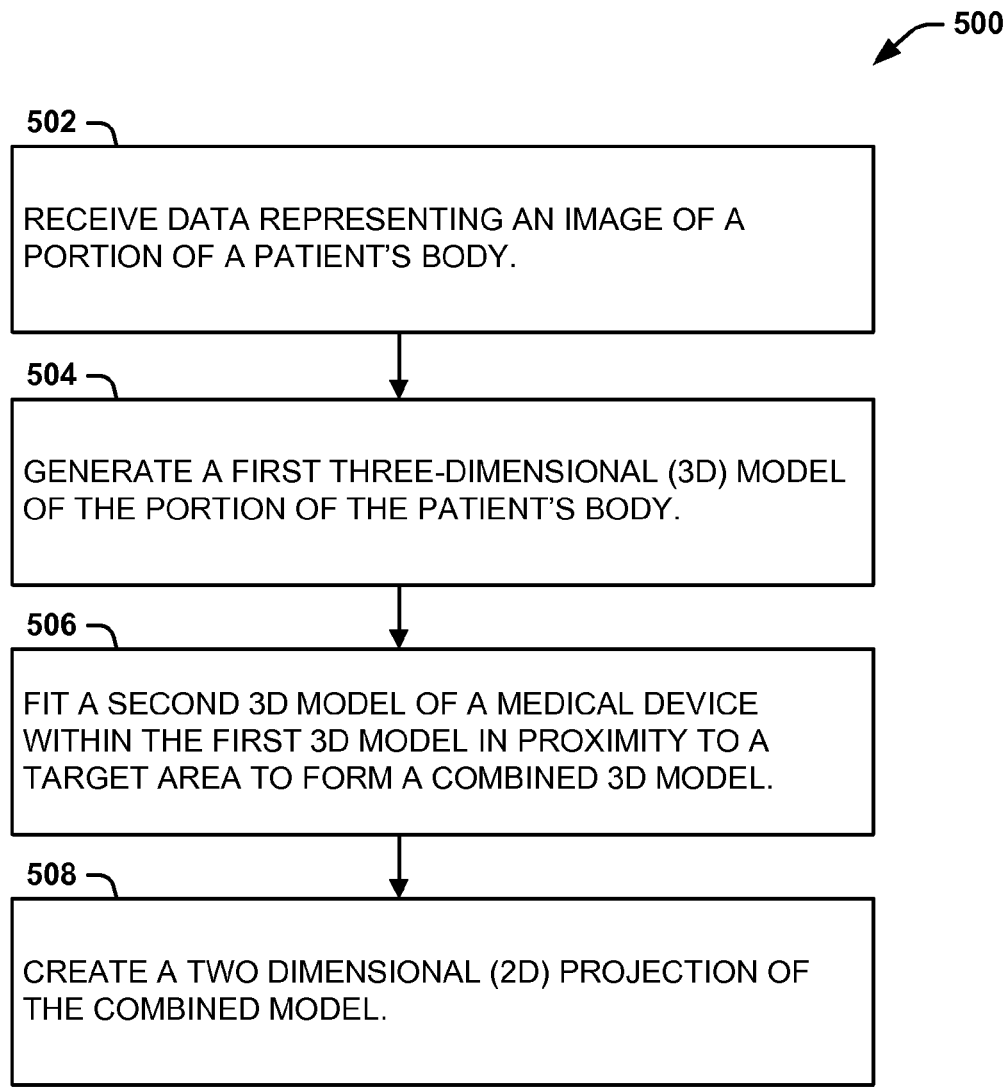
FIG. 5 is a process flow diagram illustrating a method for delivering a medical device to a location in proximity to a target region within a patient's body in accordance with another aspect of the present disclosure.

An example of a method 500 that can deliver the medical device to a location in proximity to a target region within a patient's body is shown in FIG. 5. Another example of a method 600 that can match the projection as determined by the method 500 of FIG. 5 to a real time 2D intraoperative image. A further example of a method 700 that can align the projection as determined by the method 500 of FIG. 5 with the real time 2D intraoperative image is shown in FIG. 7.

Figure 6:
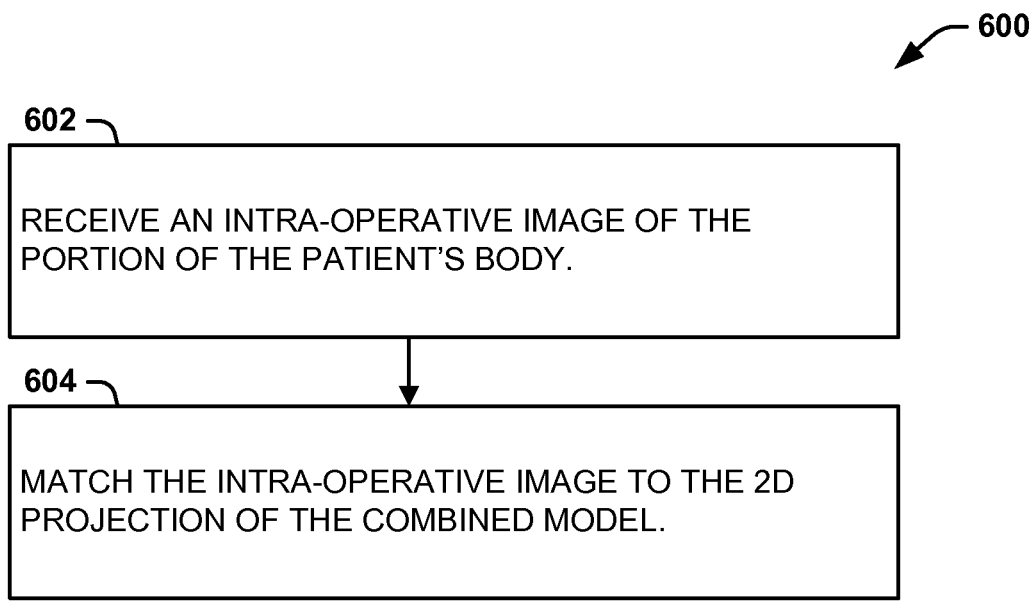
FIG. 6 is a process flow diagram illustrating a method for matching the projection as determined by the method of FIG. 5 to a real time intraoperative image.
Figure 7:
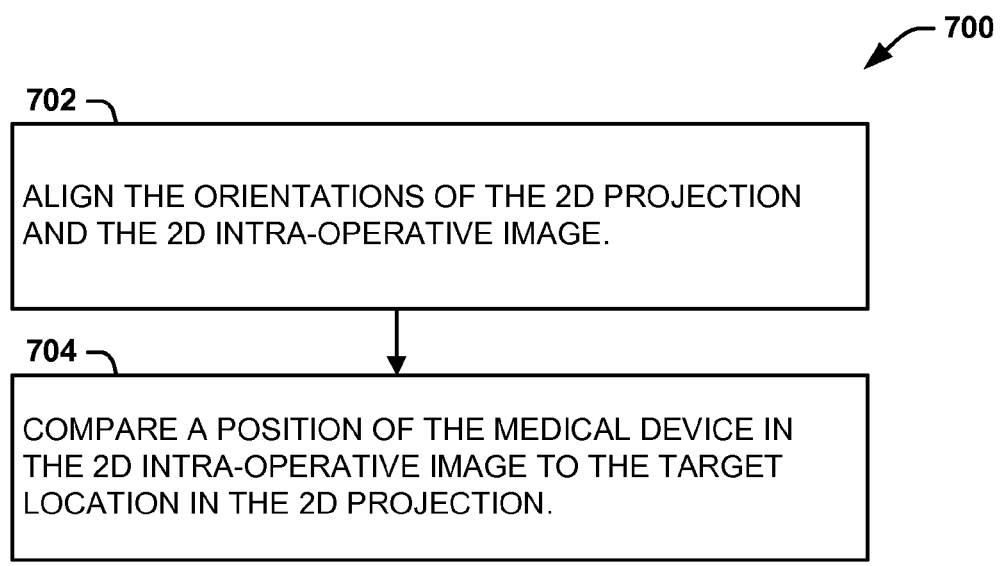
FIG. 7 is a process flow diagram illustrating a method for aligning the projection as determined by the method of FIG. 5 with the real time intraoperative image.

The methods 500, 600, and 700 of FIGS. 5, 6, and 7, respectively, are illustrated as process flow diagrams with flowchart illustrations. For purposes of simplicity, the methods 500, 600, and 700 are shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the methods 500, 600, and 700.

One or more blocks of the respective flowchart illustrations, and combinations of blocks in the block flowchart illustrations, can be implemented by computer program instructions. These computer program instructions can be stored in memory and provided to a processor of a general purpose computer, special purpose computer, and/or other programmable data processing apparatus to produce a machine, such that the instructions, which execute via the processor of the computer and/or other programmable data processing apparatus, create mechanisms for implementing the steps/acts specified in the flowchart blocks and/or the associated description. In other words, the steps/acts can be implemented by a system comprising a processor that can access the computer-executable instructions that are stored in a non-transitory memory.

The methods 500, 600, and 700 of the present disclosure may be embodied in hardware and/or in software (including firmware, resident software, micro-code, etc.). Furthermore, aspects of the present disclosure may take the form of a computer program product on a computer-usable or computer-readable storage medium having computer-usable or computer-readable program code embodied in the medium for use by or in connection with an instruction execution system. A computer-usable or computer-readable medium may be any non-transitory medium that can contain or store the program for use by or in connection with the instruction or execution of a system, apparatus, or device.

Referring to FIG. 5, an aspect of the present disclosure can include a method 500 for delivering a medical device to a location in proximity to a target region within a patient's body. In one example, the medical device can be a neurostimulator and the target region can be a region in proximity to the sphenopalatine (pterygopalatine) ganglion (SPG) located within the patient's craniofacial region. In this example, the neurostimulator can be utilized to treat pain from primary headaches.

At 502, data representing an image of a portion of the patient's body (e.g., ID) can be received (e.g., by receiver 102). The data representing the image of the portion of the patient's body that can include data representing the target region. In some instances, the image can be a standard fine resolution (e.g., less than 1 mm slice) computed tomography (CT) image of the portion of the patient's body. For example, the portion of the patient's body can include a portion of the patient's skull. When the target region is the SPG, the portion of the patient's skull can extend from the lower maxilla to the top of the frontal sinus including the entire head of the patient, including at least: the anterior maxilla, the posterior maxilla, the maxillary sinus, the zygoma, the PPF, and the pterygoid process.

At 504, a first three dimensional (3D) model of the portion of the patient's body (e.g., IM) can be generated (e.g., by 3D model generator 104) from the data representing the image. In some instances, a commercially available software package can be utilized to process the data representing the image and generate the 3D model of the portion of the patient's body represented in the image. In some instances, any preprocessing of the image data can be accomplished before creation of the 3D model of the portion of the patient's body.

Before, after, or current to the generation of the 3D model of the portion of the patient's body a 3D model of the medical device (e.g., DM) can be retrieved and/or generated (e.g., by 3D model retriever 106) based on data related to the medical device (DD). For example, the data related to the medical device can include the type of device, the size of the device, the size of components of the device, the orientation of the device, the angle of the device, etc. In some instances, the 3D model of the medical device can be generated based on the data related to the medical device. In other instances, 3D model of the medical device can be retrieved from a library including 3D models of medical devices. In some cases, retrieved 3D model of the medical device can be altered to account for features of the device data (e.g., different lead sizes).

At 506, a second 3D model of the medical device (e.g., DM) can be placed and/or fit (e.g., by fitter 108) within a first 3D model in proximity to the target region to form a combined 3D model (e.g., CM). For example, the placing and/or fitting can be based on one or more reference points common to both the 3D model of the portion of the patient's body represented in the image and the 3D model of the medical device. In some instances, the 3D model of the medical device can be fit to a plurality of different positions (also referred to as interim positions) within the 3D model of the portion of the patient's body represented in the image (IM). For example, the plurality of different positions can correspond to different sizes of the medical device, different placements of the surgical incision, different navigations through the portion of the patient's body, and/or different trajectories of the pathway from the surgical incision to the different positions.

At 508, a two dimensional (2D) projection (e.g., PP) can be created of the combined model (e.g., by 3D to 2D projector 110). In some instances, the 2D projection can include a plurality of 2D images corresponding to a complete representation of the 3D model. The 2D projection can include a plurality of projections corresponding to a rotation of the combined 3D model rotated to different angles and/or different orientations. For example, the 2D projection can be rotated to provide views, including at least an anterior-posterior (AP) view and a lateral (profile) view. In some instances, when the image or the portion of the patient's body is a CT image, the 2D projection can be a digitally reconstructed radiograph (DRR). For example, a DRR can be created using a software program, such as the open source Visualization Toolkit.

A surgeon can utilize the 2D projection for navigation and/or delivery of the medical device to the target region. For example, the 2D projection can include one or more bone landmarks. In some instances, the 2D projection can act as a guide or map for the surgeon in the placement of the medical device. In other instances, the 2D projection can be used to facilitate the navigation and delivery of the device.

As shown in FIG. 6, the 2D projection can be used in a method 600 for matching the 2D projection (e.g., PP) to a real time 2D intraoperative image (e.g., II). For example, the real time 2D intraoperative image can be a fluoroscopic image that can be taken during an operation to implant the medical device.

At 602, the 2D intraoperative image of the portion of the patient's body can be received (e.g., by 2D to 2D matcher 302). At 604, the intraoperative image can be matched to the 2D projection of the combined model. For example, the intraoperative image can be correlated to the 2D projection using one or more bone landmarks common to both images.

In some instances, the 2D projection and the real time 2D intraoperative image can both be displayed to facilitate comparison. The comparison can tell how close the actual medical device position is to the planned position in proximity to the target region. In some instances, the 2D projection (PP) and the real time 2D intraoperative image can be displayed as separate images. For example, the two images can be displayed side-by-side. In other instances, the 2D projection (PP) and the real time 2D intraoperative image (II) can be displayed with one image overlaid on the other image.

In some instances, a real time 2D intraoperative image with the actual medical device in the patient's body can be created during the surgical procedure and back projected onto the 3D combined model or the 3D model of the portion of the patient's body represented in the image to transfer the location of the medical device from the real time 2D intraoperative image to the 3D combined model or the 3D model of the portion of the patient's body represented in the image. The 3D model of the medical device can be displayed at the actual location of the medical device to facilitate delivery of the medical device to the planned position in proximity to the target region.

A method 700 for aligning the 2D projection with the real time 2D intraoperative image is shown in FIG. 7. The aligning can facilitate the overlaying of the images on top of one another to facilitate the delivery of the medical device to the planned position.

At 702, orientations of the 2D projection (e.g., PP) and the 2D intraoperative image (e.g., II) can be aligned (e.g., by aligner 402). The real time 2D intraoperative image can be aligned with the 2D projection (or vice versa). The alignment can be based on one or more bone landmarks that are present in both the 2D projection and the real time 2D intraoperative image. For example, the combined 3D model can be rotated in three dimensions to create a second 2D projection to match the 2D fluoroscopic image of the portion of the patient's body. In this case, each different 2D projection can correspond to a different orientation, and each of the different 2D projections can be fit to the real time 2D intraoperative image. This can facilitate the matching of the orientation of the 2D projection (e.g., APP) to the real time 2D intraoperative image (e.g., AII).

At 704, a position of the medical device in the 2D intraoperative image (e.g., AII) can be compared (e.g., by comparator 404) to the target location in the 2D projection (e.g., APP). Based on the comparison, a graphic can be output that indicates that the planned position has been reached, the number of millimeters until the planned position is reached, and/or a trajectory to reach the planned location.

From the above description, those skilled in the art will perceive improvements, changes and modifications. Such improvements, changes and modifications are within the skill of one in the art and are intended to be covered by the appended claims.

What is claimed is:

1. A system comprising:
   a non-transitory memory storing computer-executable instructions; and
   a processor that executes the computer-executable instructions to at least:
      generate a three dimensional (3D) patient-specific digital model of an anatomical region of interest of a patient's body from a series of 2D images taken before surgery;
      fit another 3D digital model of a neurostimulator into the anatomical region of interest in the 3D patient-specific digital model, wherein the other 3D model of the neurostimulator is selected from a library of different neurostimulator shapes, lengths, and anatomical specifications;
      create a combined 3D digital model based on the other 3D digital model merged into the anatomical region of interest in the 3D patient-specific digital model; and
      create a series of 2D projections of the combined 3D digital model, which are used during surgery and compared to a 2D intraoperative image to accurately place the neurostimulator within the anatomical region of interest.

2. The system of claim 1, wherein the at least one of the series of 2D projections is matched to the 2D intraoperative image according to at least one landmark common between the at least one of the series of 2D projections and the intraoperative image.

3. The system of claim 2, wherein the at least one landmark corresponds to at least one bone structure within the anatomical region of interest of the patient's body.

4. The system of claim 1, wherein the 2D intraoperative image is a fluoroscopic image.

5. The system of claim 1, wherein the anatomical region of interest comprises the sphenopalatine ganglion (SPG) within the patient's skull.

6. The system of claim 5, wherein the portion of the patient's skull comprises at least one of: the anterior maxilla, the posterior maxilla, the maxillary sinus, the zygoma, the pterygopalatine fossa (PPF), and the pterygoid process.

7. A method comprising the steps of:
   generating, by a system comprising a processor, a three-dimensional (3D) patient-specific digital model of an anatomical region of interest of a patient's body from a series of two-dimensional (2D) images taken before surgery;
   fitting, by the system, another 3D digital model of a neurostimulator into the anatomical region of interest in the 3D patient-specific digital model to create a combined 3D digital model, wherein the other 3D digital model of the neurostimulator is selected from a library of different neurostimulator shapes, lengths, and anatomical specifications; and
   creating, by the system, a series of new 2D images from the combined 3D digital model, which are used during surgery to accurately place the neurostimulator within the anatomical region of interest of the patient's body.

8. The method of claim 7, further comprising comparing, by the system, at least a portion of the series of new 2D images to intra-operative 2D images of the anatomical region of interest of a patient's body to ensure accurate placement of the neurostimulator within the region of interest.

9. The method of claim 8, wherein the comparing further comprises matching at least the portion of 2D images to the intra-operative 2D images according to at least one common landmark.

10. The method of claim 9, wherein the at least one common landmark corresponds to at least one bone structure within the portion of the patient's body.

11. The method of claim 8, wherein the intraoperative 2D images are fluoroscopic images.

12. The method of claim 7, wherein the series of 2D images are taken from a computed tomography (CT) image of the anatomical region of interest of the patient's body, and wherein each of the 2D images comprises a digitally reconstructed radiograph (DRR) projection of the combined 3D digital model.

13. The method of claim 7, wherein the anatomical region of interest of the patient's body comprises a portion of the patient's skull; and
   wherein a target region for delivery of the neurostimulator comprises the sphenopalatine ganglion (SPG).

14. The method of claim 13, wherein the portion of the patient's skull comprises at least one of: the anterior maxilla, the posterior maxilla, the maxillary sinus, the zygoma, the pterygopalatine fossa (PPF), and the pterygoid process.

* * * * *